United States Patent
Maguire et al.

(10) Patent No.: US 10,730,994 B2
(45) Date of Patent: Aug. 4, 2020

(54) SYNTHESIS OF POLYCARBONATE SILOXANE DIOLS

(71) Applicants: Aortech International plc, Weybridge, Surrey (GB); Francis P. Maguire, Salt Lake City, UT (US); Sriram Venkataramani, Draper, UT (US)

(72) Inventors: Francis P. Maguire, Salt Lake City, UT (US); Sriram Venkataramani, Draper, UT (US)

(73) Assignee: Aortech International plc, Weybridge (GB)

(*) Notice: Subject to any disclaimer, the term of this patent is extended or adjusted under 35 U.S.C. 154(b) by 80 days.

(21) Appl. No.: 15/735,054

(22) PCT Filed: Jun. 8, 2016

(86) PCT No.: PCT/US2016/036468
§ 371 (c)(1),
(2) Date: Dec. 8, 2017

(87) PCT Pub. No.: WO2016/200958
PCT Pub. Date: Dec. 15, 2016

(65) Prior Publication Data
US 2018/0179324 A1    Jun. 28, 2018

Related U.S. Application Data

(60) Provisional application No. 62/172,657, filed on Jun. 8, 2015.

(51) Int. Cl.
| | | |
|---|---|---|
| *C08G 18/61* | (2006.01) | |
| *A61L 31/06* | (2006.01) | |
| *A61L 15/26* | (2006.01) | |
| *C08G 64/02* | (2006.01) | |
| *C08G 64/30* | (2006.01) | |
| *A61L 27/18* | (2006.01) | |
| *A61L 29/06* | (2006.01) | |
| *C08G 64/18* | (2006.01) | |
| *C08G 77/448* | (2006.01) | |

(52) U.S. Cl.
CPC ............ *C08G 18/615* (2013.01); *A61L 15/26* (2013.01); *A61L 27/18* (2013.01); *A61L 29/06* (2013.01); *A61L 31/06* (2013.01); *C08G 64/0266* (2013.01); *C08G 64/186* (2013.01); *C08G 64/305* (2013.01); *C08G 77/448* (2013.01)

(58) Field of Classification Search
CPC .. C08G 18/615; C08G 18/61; C08G 18/6469; C08G 77/448
See application file for complete search history.

(56) References Cited

U.S. PATENT DOCUMENTS

| | | | | |
|---|---|---|---|---|
| 4,131,731 A * | 12/1978 | Lai | ......................... | C08G 18/44 528/370 |
| 5,550,169 A * | 8/1996 | Yata | .................... | C08G 18/4063 521/112 |
| 6,313,254 B1 * | 11/2001 | Meijs | ..................... | A61L 15/26 428/15 |
| 2003/0092864 A1 * | 5/2003 | Gunatillake | ....... | C08G 18/4692 528/26 |
| 2004/0054113 A1 * | 3/2004 | Benz | ..................... | C08G 18/10 528/10 |
| 2011/0086940 A1 * | 4/2011 | Rega | ..................... | A61L 27/18 523/122 |

FOREIGN PATENT DOCUMENTS

| | | |
|---|---|---|
| EP | 0938512 A1 | 9/1999 |
| EP | 0984997 A1 | 3/2000 |

OTHER PUBLICATIONS

International Application Serial No. PCT/US2016/036468, International Search Report and Written Opinion dated Jul. 28, 2016, 9 pgs.
"European Application Serial No. 16730977.2, Response filed Jul. 31, 2018 to Communication pursuant to Rules 161(1) and 162 EPC dated Jan. 30, 2018", 7 pgs.
"International Application Serial No. PCT/US2016/036468, International Preliminary Report on Patentability dated Dec. 21, 2017", 7 pgs.
Australian Application Serial No. 2016274606, First Examination Report dated Dec. 4, 2019, 3 pgs.
European Application Serial No. 16730977.2, Communication Pursuant to Article 94(3) EPC dated Jan. 7, 2020, 3 pgs.
"European Application Serial No. 16730977.2, Response filed Mar. 18, 2020 to Communication Pursuant to Article 94(3) EPC dated Jan. 7, 2020", 11 pgs.
Australian Application Serial No. 2016274606, Response filed Apr. 3, 2020 to First Examination Report dated Dec. 4, 2019, 13 pgs.

* cited by examiner

*Primary Examiner* — Michael M Dollinger
(74) *Attorney, Agent, or Firm* — Schwegman Lundberg & Woessner, P.A.

(57) ABSTRACT

The present invention provides silicon-based polycarbonates, processes for their preparation and their use in the synthesis of copolymers, in particular segmented copolymers such as polyurethanes for biomedical applications.

8 Claims, No Drawings

SYNTHESIS OF POLYCARBONATE SILOXANE DIOLS

CLAIM OF PRIORITY

This application is a U.S. National Stage Filing under 35 U.S.C. 371 from International Application No. PCT/US2016/036468, filed on Jun. 8, 2016, and published as WO 2016/200958 A1 on Dec. 15, 2016, which claims the benefit of priority under 35 U.S.C. § 119(e) to U.S. Provisional Patent Application No. 62/172,657, filed on Jun. 8, 2015, each of which is incorporated by reference herein in its entirety.

BACKGROUND OF THE INVENTION

Segmented copolymers typically derive good mechanical properties from the separation of microphases caused by immiscibility of the segments. For example, it is known that in thermoplastic polyurethane elastomers, the so-called "hard" and "soft" segments have limited miscibility and separate to form microdomains. Many of the properties of polyurethane elastomers can be rationalized in terms of a semi-crystalline hard domain providing a reinforcement or filler-like effect within a soft matrix. The soft matrix or domain, most frequently comprises a poly(alkylene ether) or polyester chain of molecular weight within the range of about 500 to 2000. Such short polymer chains are generally terminated with hydroxyl groups and known as "macrodiols".

The structure of the macrodiol plays a significant role in determining the performance of the segmented copolymer. Polyester-based macrodiols generally give good mechanical properties, but poor resistance to degradation in harsh environments experienced in for example marine and biomedical applications.

Polyether macrodiols offer enhanced stability, but are not suitable for the synthesis of extremely soft materials, particularly when high stability is also required.

Polysiloxane-based polymers, especially polydimethyl siloxane (PDMS) exhibit characteristics such as low glass transition temperatures, good thermal, oxidative and hydrolytic stabilities and low surface energies. These properties would be desirable in the macrodiol-derived component of a segmented copolymer. In addition, they display good compatibility with biological tissues and fluids and low toxicity. For these reasons, PDMS has found particular application in the construction of medical devices, especially implantable devices. However, polymers derived from PDMS do not generally exhibit good tensile properties such as flexural strength or abrasion resistance.

Considerable efforts have gone into finding a means for incorporating low molecular weight PDMS segments into segmented copolymers such as polyurethanes. These efforts have mainly focused on achieving clarity, processability and a good balance of mechanical properties. However, no completely successful attempts have been disclosed.

As a result of large differences in solubility parameters of PDMS and most conventional hard segments, PDMS-based polyurethanes are likely to be highly phase separated materials characteristic of poor mechanical properties. As a result of this large difference in polarity between hard and soft segments, it is anticipated that premature phase separation occurs during synthesis and there is compositional heterogeneity and overall low molecular weight. In addition, there appears to be an optimal degree of mixing at the interface between soft and hard domains, with extremely sharp interfaces leading to a low degree of mechanical coupling between the two domains and resulting poor strength. Thus it is understood that, for example, PDMS-based polyurethanes generally exhibit poor mechanical properties. Typically, the tensile strength and elongation at break are about 7 MPa and 200%, respectively.

Polycarbonate macrodiols have also been used as reactive ingredients in the synthesis of block and segmented copolymer systems, in particular high performance polyurethanes. Processes for preparing polycarbonate macrodiols based on a range of bishydroxy alkylene compounds are disclosed in JP 62,241,920 (Toa Gosei Chemical Industry Co. Ltd.), JP 64,01,726 (Dainippon Ink and Chemicals, Inc.), JP 62,187,725 (Daicel Chemical Industries, Ltd.) DE 3,717,060 (Bayer A. G.), U.S. Pat. No. 4,105,641 (Bayer Aktiengesellschaft), U.S. Pat. No. 4,131,731 (Beatrice Foods Company) and U.S. Pat. No. 5,171,830 (Arco Chemical Technology). The most common alkylenediol described in these patent specifications is 1,6-hexanediol.

Although polycarbonate macrodiols are generally classified under polyesters, the corresponding polyurethanes exhibit hydrolytic stabilities comparable or in some cases superior to polyetherurethanes. They also possess high tensile strength and toughness. These properties are attributed to the high level of phase mixing, promoted by intermolecular hydrogen bonding involving the hard segment urethane hydrogens and the carbonate functional groups of the soft segment. The hydrogen bonding is also partly responsible for the relatively poor elastomeric properties such as low flexibility and high durometer hardness of polyurethanes based on polycarbonate macrodiols. These properties are in contrast to those of the non-polar macrodiol based polyurethanes, such as those based on siloxanes.

A need accordingly exists to develop silicon-based macrodiols for use as building blocks of segmented copolymers such as polyurethanes with structural features that exhibit good compatibility and mechanical properties. Suitable macrodiols would retain the advantages of silicon-based polymers such as flexibility, low temperature performance, stability and in some cases biocompatibility. The disadvantages of poor mechanical properties is to be avoided so that the silicon-based macrodiols can form part of materials which can be used in various demanding applications, particularly the biomedical field.

SUMMARY OF THE INVENTION

Polycarbonate siloxane macrodiols have normally been prepared in a single-stage transesterication reaction. The novel two-stage process of the invention allows wider range of raw materials to be used and reduces the level of by-products. The process to prepare polycarbonate-siloxane macrodiols proceeds via a two stage process. Such compounds are the subject of U.S. Pat. No. 7,026,423, which is incorporated by reference herein.

The first stage represents the condensation polymerization of the diethyl carbonate (DEC) and the bis(hydroxybutyl) tetramethyldisiloxane (BHTD) moiety. Second stage polymerisation involves the progressive increase of temperature and reduction of reaction pressure (from about 600 Torr to about 1 Torr) necessary to remove polycondensation by-products and subsequently to increase the molecular weight of the polyol product.

DETAILED DESCRIPTION OF THE INVENTION

According to one aspect of the present invention there is provided a silicon-based polycarbonate of the formula (I):

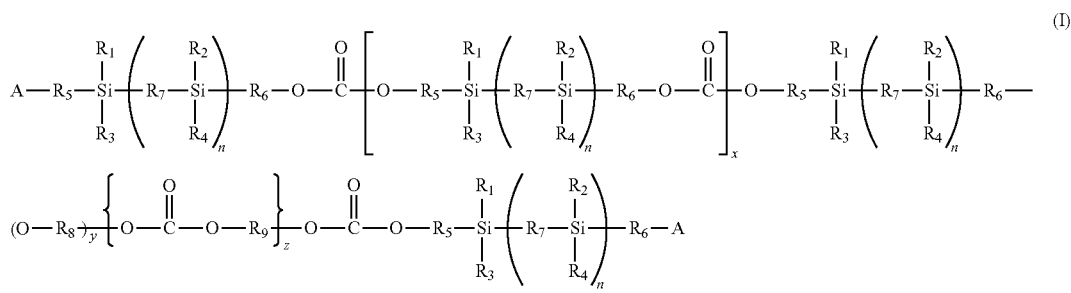

wherein

R₁, R₂, R₃, and R₄ are the same or different and can be hydrogen or an optionally substituted straight chain, branched or cyclic, saturated or unsaturated hydrocarbon radical;

R₅, R₆, R₈ and R₉ are the same or different and can be an optionally substituted straight chain, branched or cyclic, saturated or unsaturated hydrocarbon radical;

R₇ is a divalent linking group or an optionally substituted straight chain, branched or cycle, saturated or unsaturated hydrocarbon radical;

A is an end capping group;

n, y and z are integers of 0 or more; and x is an integer of 0 or more.

The hydrocarbon radical for substituents R₁, R₂, R₃ and R₄ may include alkyl, alkenyl, alkynyl, aryl or heterocyclyl radicals. It will be appreciated that the equivalent radicals may be used for substituents R₅, R₆, R₇, R₈ and R₉ except that the reference to alkyl, alkenyl and alkynyl should be to alkylene, alkenylene and alkynylene, respectively. In order to avoid repetition, only detailed definitions of alkyl, alkenyl and alkynyl are provided hereinafter.

The term "alkyl" denotes straight chain, branched or mono- or poly-cyclic alkyl, preferably C₁₋₁₂alkyl or cycloalkyl. Examples of straight chain and branched alkyl include methyl, ethyl, propyl, isopropyl, butyl, isobutyl, sec-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3-, or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like.

The term "alkenyl" denotes groups formed from straight chain, branched or mono- or poly-cyclic alkenes including ethylenically mono- or poly-unsaturated alkyl or cycloalkyl groups as defined above, preferably C₂₋₁₂alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3 heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" denotes groups formed from straight chain, branched, or mono- or poly-cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl" denotes mono- or poly-cyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered hetermonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl , alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

Preferably z is an integer of 0 to about 50 and x is an integer of 1 to about 50. Suitable values for n include 0 to about 20, more preferably 0 to about 10. Preferred values for y are 0 to about 10, more preferably 0 to about 2.

The term "end capping group" is used herein in its broadest sense and includes reactive functional groups or groups containing reactive functional groups. Suitable examples of reactive functional groups are alcohols, carboxylic acids, aldehydes, ketones, esters, acid halides, acid anhydrides, amines, imines, thio, thioesters, sulphonic acid and epoxides. Preferably the reactive functional group is an alcohol or an amine, more preferably an alcohol.

A preferred polycarbonate is a compound of the formula (I) wherein A is OH which is a polycarbonate macrodiol (a polycarbonate siloxane diol) of the formula (1a):

the polycarbonate macrodiol is about 400 to about 5000, more preferably about 400 to about 2000.

The present invention also provides a process for preparing the silicon-based polycarbonate macrodiol of the formula (Ia) as defined above which includes reacting a source of carbonate with either:

(i) a silicon-based diol of the formula (II)

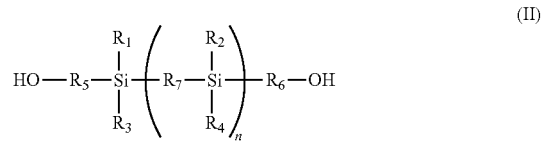

wherein
$R_1$ to $R_7$ and n are as defined in formula (Ia) above; or
(ii) the silicon-based diol of the formula (II) defined in (i) above and a non-silicon based diol of the formula (III):

HO—$R_9$—OH     (III)

wherein
$R_9$ is as defined above in formula (Ia).

This process may be extended to the preparation of the silicon-based polycarbonate of the formula (I) by including the additional step of converting the hydroxyl groups in the macrodiol of the formula (1a) into other reactive functional groups. This conversion step can be achieved using procedures known in the art such as oxidation to give a dicarboxylic acid, conversion to an amine using the Gabriel procedure or reaction with an end capping agent for example, diisocyanate, dicarboxylic acid, cyclic anhydride or the like.

The source of carbonate may be a carbonate compound or two or more reagents which when combined produce carbonate or a carbonate compound. It will be appreciated that

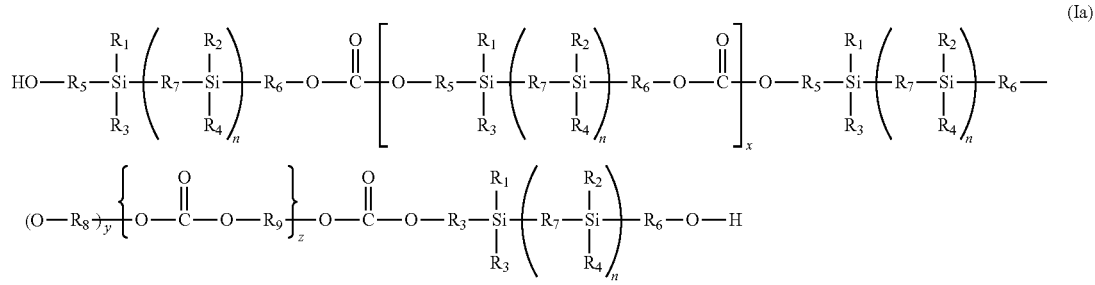

wherein
$R_1$ to $R_6$, $R_8$, $R_9$, n, y, x and z are as defined in formula (I) above and $R_7$ is a divalent linking group or an optionally substituted straight chain, branched or cyclic, saturated or unsaturated hydrocarbon radical;

Suitable divalent linking groups for $R_7$ include O, S and NR wherein R is hydrogen or an optionally substituted straight chain, branched or cyclic, saturated or unsaturated hydrocarbon radical.

Particularly preferred polycarbonate macrodiols are compounds of the formula (Ia) wherein $R_1$, $R_2$, $R_3$ and $R_4$ are methyl, $R_8$ is ethyl, $R_9$ is hexyl, $R_5$ and $R_6$ are propyl or butyl and $R_7$ is O or —$CH_2$—$CH_2$—, more preferably $R_5$ and $R_6$ are propyl when $R_7$ is O and $R_5$ and $R_6$ are butyl when $R_7$ is —$CH_2$—$CH_2$—. The preferred molecular weight range of the source of carbonate will include the $R_8$ substituent. Suitable carbonate compounds include cyclic carbonates such as alkylene carbonates, for example ethylene or propylene carbonate and linear carbonates such as diallyl or diaryl carbonates, for example, dimethyl carbonate, diethyl carbonate or diphenyl carbonate. Preferably the source of carbonate has a low molecular weight because of the ease of removal of the condensation by-product from the reaction mixture.

The silicon-based diols of the formula (II) can be obtained as commercially available products. For example 1,3-bis-hydroxypropyl-1,1,3,3-tetramethyldisiloxane and 1,3-bishydroxybutyl-1,1,3,3-tetramethyldisiloxane are available from Shin Etsu or Silar Laboratories. Others can be prepared by using the appropriate disilane compounds and hydroxy terminated olefinic compounds using a hydrosilylation reaction.

It will be appreciated that the diol of formula (II) can be used separately or as a mixture containing two or more structurally different diols in the preparation of the polycarbonates according to the present invention. The presence of silicon or siloxy radicals in the diol imparts hydrophobic and flexibility characteristics which results in improved elastomeric and degradation resistance in copolymers produced using these polycarbonates.

In another embodiment, non-silicon based diols of the formula (III) can be used in combination with the silicon-based diols of the formula (II) for the preparation of polycarbonates. Preferably, the non-silicon based diol is an aliphatic dihydroxy compound, such as, alkylene diols, for example, 1,4-butanediol, 1,6-hexanediol, diethyleneglycol, triethyleneglycol, 1,4-cyclohexanediol or 1,4-cyclohexanedimethanol. It has been found that when a silicon-containing diol and an alkylene diol are reacted, the resulting polycarbonate is generally a random copolycarbonate. Accordingly, polycarbonates having a broad range of properties can be prepared by choosing different ratios of the two diols.

The process for preparing the polycarbonate is preferably a transesterification similar to that described in U.S. Pat. No. 4,131,731 which is carried out in the presence of a transesterification catalyst. Examples of suitable catalysts include those disclosed in U.S. Pat. No. 4,105,641 such as stannous octoate and dibutyl tin dilaurate.

It will be appreciated that other processes may be used to prepare the polycarbonate of the present invention such as those described by Eckert et al[5] which are incorporated herein by reference. Some of these processes include reacting the source of carbonate and the diol of the formula (II) with either phosgene (ClCOCl) or chloroformates, for example, Cl—COO—R'—OCOCl wherein R' is a divalent linking group or an optionally substituted straight chain, branched or cyclic, saturated or unsaturated hydrocarbon radical.

The polycarbonate of the present invention may be used in the preparation of copolymers such as copolyesters, copolyethercarbonates, copolyamides, copolyimides or segmented copolymers for example polyurethane or polyurethane urea elastomers.

Thus, the present invention further provides a copolymer which includes a silicon-based polycarbonate segment of the formula (Ib):

According to a still further aspect of the present invention there is provided a polyurethane elastomeric composition which includes a silicon-based polycarbonate segment of the formula (Ib) defined above where $R_7$ is a divalent linking group or an optionally substituted straight chain, branched or cyclic, saturated or unsaturated hydrocarbon radical.

The polyurethane elastomeric compositions of the present invention may be prepared by any suitable technique. A preferred method involves mixing the polycarbonate and a chain extender and then reacting this mixture with a diisocyanate. The initial ingredients are preferably mixed at a temperature in the range of about 45 to about 100° C. more preferably about 60 to about 80° C. If desired, a catalyst such as dibutyl tin dilaurate at a level of about 0.001 to about 0.5 wt % based on the total ingredients may be added to the initial mixture. The mixing may occur in conventional apparatus or within the confines of a reactive extruder or continuous reactive injection molding machine.

Alternatively, the polyurethanes may be prepared by the prepolymer method which involves reacting a diisocyanate with the polycarbonate to form a prepolymer having terminally reactive diisocyanate groups. The prepolymer is then reacted with a chain extender.

Thus, the polyurethane elastomeric composition of the present invention may be further defined as comprising a reaction product of:

(i) a silicon-based polycarbonate of the formula (I) defined above where $R_7$ is a divalent linking group or an optionally substituted straight chain, branched or cyclic, saturated or unsaturated hydrocarbon radical;

(ii) a diisocyanate; and (iii) a chain extender.

Preferably, the diisocyanate is selected from 4,4'-methylenediphenyl diisocyanate (MDI), methylene bis (cyclohexyl) diisocyanate (H12MDI), p-phenylene diisocyanate (p-PDI), trans-cyclohexane-1,4-diisocyanate (CHDI) or a mixture of the cis and trans isomers, 1,6-hexamethylene diisocyanate (DICH), 2,4-toluene diisocyanate (2,4-TDI) or its isomers or mixtures thereof, p-tetramethylxylene diisocyanate (p-TMXDI) and m-tetramethylxylene diisocyanate (m-TMXDI). MDI is particularly preferred.

The chain extender is preferably selected from 1,4butanediol, 1,6-hexanediol, 1,8-octanediol, 1,9-nonanediol, 1,10-decanediol 1,4-cyclohexane dimethanol, p-xyleneglycol, 1,4-bis (2-hydroxyethoxy) benzene and 1,12-dodecanediol, 1,4-butanediol is particularly preferred.

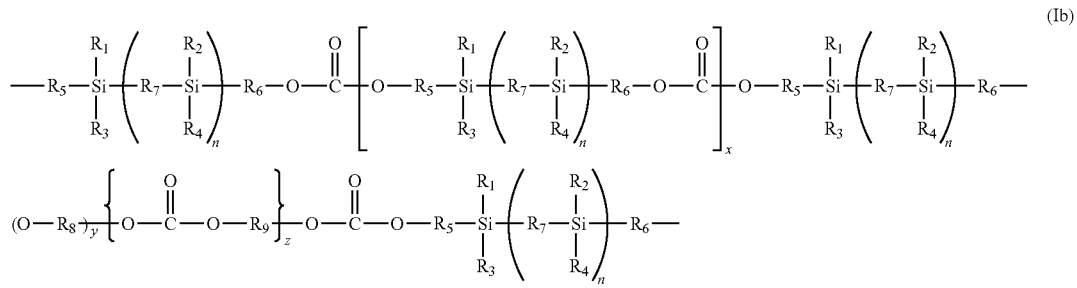

wherein $R_1$ to $R_9$, n, y, x and z are as defined in formula (I) above.

The polycarbonate of the present invention is particularly useful in preparing polyurethane elastomeric compositions.

A particularly preferred polyurethane elastomeric composition of the present invention comprises a reaction product of:

(i) compounds of the formula (Ia) wherein $R_1$, $R_2$, $R_3$ and $R_4$ are methyl, $R_8$ is ethyl, $R_9$ is hexyl, $R_5$ and $R_6$ are propyl or butyl and $R_7$ is O or —$CH_2$—$CH_2$—.

(ii) MDI; and (iii) 1,4-butanediol.

An advantage of the incorporation of the polycarbonate segment is the relative ease of processing of the polyurethane by conventional methods such as extrusion, injection and compression moulding without the need of added processing waxes. If desired, however, conventional polyurethane processing additives such as catalysts, antioxidants, stabilizers, lubricants, dyes, pigments, inorganic and/or organic fillers and reinforcing materials can be incorporated into the polyurethane during preparation. Such additives are preferably added to the polycarbonate.

The polycarbonate, diisocyanate and chain extender may be present in certain proportions. The preferred level of hard segment (i.e., diisocyanate and chain extender) in the composition is about 30 to about 60 wt %, more preferably 40 to 50 wt %.

The polyurethane elastomeric composition of the present invention is particularly useful in preparing materials having good mechanical properties, in particular biomaterials.

According to another aspect of the present invention there is provided a material having improved mechanical properties, clarity, processability and/or degradation resistance comprising a polyurethane elastomeric composition which includes a polycarbonate segment of the formula (Ib) defined above.

The present invention also provides use of the polyurethane elastomeric composition defined above as a material having improved mechanical properties, clarity, processability and/or degradation resistance.

The present invention further provides the polyurethane elastomeric composition defined above when used as a material having improved mechanical properties, clarity, processability and/or degradation resistance.

The mechanical properties which are improved include tensile strength, tear strength, abrasion resistance, Durometer hardness, flexural modulus and related measures of flexibility or elasticity.

The improved resistance to degradation includes resistance to free radical, oxidative, enzymatic and/or hydrolytic processes and to degradation when implanted as a biomaterial.

The improved processability includes ease of processing by casting such as solvent casting and by thermal means such as extrusion and injection molding, for example, low tackiness after extrusion and relative freedom from gels.

There is also provided a degradation resistant material which comprises the polyurethane elastomeric composition defined above.

The polyurethane elastomeric composition of the present invention shows good elastomeric properties. It should also have a good compatibility and stability in biological environments, particularly when implanted in vivo for extended periods of time.

According to another aspect of the present invention there is provided an in vivo degradation resistant material which comprises the polyurethane elastomeric composition defined above.

The polyurethane elastomeric composition may also be used as a biomaterial. The term "biomaterial" is used herein in its broadest sense and refers to a material which is used in situations where it comes into contact with the cells and/or bodily fluids of living animals or humans.

The polyurethane elastomeric composition is therefore useful in manufacturing medical devices, articles or implants.

Thus, the present invention still further provides medical devices, articles or implants which are composed wholly or partly of the polyurethane elastomeric composition defined above.

The medical devices, articles or implants may include cardiac pacemakers and defibrillators, catheters, cannulas, implantable prostheses, cardiac assist devices, heart valves, vascular grafts, extra-corporeal devices, artificial organs, pacemaker leads, defibrillator leads, blood pumps, balloon pumps, A-V shunts, biosensors, membranes for cell encapsulation, drug delivery devices, wound dressings, artificial joints, orthopedic implants and soft tissue replacements.

It will be appreciated that polyurethane elastomeric compositions having properties optimized for use in the construction of various medical devices, articles or implants will also have other non-medical applications. Such applications may include their use in the manufacture of artificial leather, shoe soles; cable sheathing; varnishes and coatings; structural components for pumps, vehicles, etc; mining ore screens and conveyor belts; laminating compounds, for example in glazing; textiles; separation membranes; sealants or as components of adhesives.

It will also be understood that the siloxane component of the polyurethane elastomeric composition by virtue of its dielectric properties will provide opportunities for use in electronic and electrical components and insulation.

Thus, the present invention extends to the use of the polyurethane elastomeric composition defined above in the manufacture of devices or articles.

The present invention also provides devices or articles which are composed wholly or partly of the polyurethane elastomeric composition defined above.

EXAMPLES

Example 1

Preparation of Polycarbonate Siloxane Diol (Ia)

A. Raw Materials

Diethylcarbonate (anhydrous 99%), Titanium tetrabutoxide (TBT) (reagent grade 97%), Deionized water, Dichloromethane (chrome AR), Sodium sulphate (Anhydrous granular 99%), Activated charcoal were used as received. Bishydroxybutyltetramethyldisiloxane (BHTD) was purified before use.

B. Raw Material Purification

One of the raw materials, BHTD received from supplier needs to be purified. In the BHTD synthesis, ethyl iodide and iodine were used. Even traces of iodine present in BHTD can interfere with the synthesis. To remove the iodine from BHTD, activated charcoal was used. The charcoal helps to purify the raw materials before being used for Polyol synthesis. To do this, a 2% w/w activated charcoal was added to BHTD and stirred for 24 h. The resulting charcoal slurry was then filtered, under nitrogen, through a 50μ Eaton filter bag and 0.45μ cartridge filter. The resulting once charcoal treated BHTD was, again, treated with 2% charcoal and allowed to stir for 24 h then filtered through a 0.45μ filter. The approximate loss of each charcoal treatment was 10%.

C. First Stage (1 Kg Batch):

BHTD (813.66 g, 1 M) and Titanium tetrabutoxide (TBT) (4.07 g, 0.5% of BHTD) were placed in a 2 L three neck round bottom flask, equipped with mechanical stirrer, fractionating column and Liebig condenser. The temperature of the oil bath was raised to 130° C. and diethyl carbonate (186.34, 0.54M), was added using peristaltic pump over a period of 1 h. The reaction continued for a further 1 h under reflux at same temperature and stirred at 150 rpm.

D. Second Stage:

After 1 h reflux, the Liebeg condenser was connected to the fractionating column at one end and 1 L RB flask on the other end to distill of the by-product and azeotropic mixture. Then the temperature was gradually raised to 150° C. while increasing the vacuum to 1 Torr, stepwise. At regular intervals of time, change temperature, vacuum and remove distillate. In the final stage after second decant, the whole reaction mixture is refluxed at 150° C. at 1 Tor for a 1 h. Then the reaction was stopped and cooled to room temperature (about 20-30° C.), to yield a crude polycarbonate siloxane diol of m.w. 520-650.

E. Catalyst Inactivation:

To inactivate the catalyst, to the cooled crude polycarbonate siloxane diol, deionized water (20% of batch scale) was added. The mixture is refluxed for 1 h at 130° C. Distilled off the water by increasing the vacuum from about 200 to 1 Torr at regular intervals of time. The final product was cooled and dissolved in dichloromethane to make a 50% solution. The solution was vacuum filtered through Sodium Sulphate bed and subjected to charcoal treatment (2% w/w, batch size) overnight at room temperature. After 24 h, pressure filtered through 50μ Eaton bag filter and 0.45+0.2μ Sartorius cartridge filter under nitrogen.

F. Stripping:

The filtered polycarbonate siloxane diol in dichloromethane was stripped twice using 2" stripper. First stripping was at 70° C. at 15 ml/min to remove the solvent under vacuum. The second stripping at 145° C. at 4 ml.min to remove the traces of solvent and lower molecular weight fractions. The stripped polycarbonate siloxane diol was tightly sealed and stored at room temperature. The yield was ~65%. The molecular weight was about 600.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method of preparing a polycarbonate siloxane macrodiol, comprising:
    (a) preparing a reaction mixture consisting of a carbonate source, a bis(hydroxy $C_3$-$C_4$ alkyl)tetramethyldisiloxane, and an initiator catalyst, at a temperature of about 120-140° C.;
    (b) heating the reaction mixture at about 120-140° C., with stirring for about 0.5-2.0 hours at atmospheric pressure;
    (c) raising the temperature of the heated reaction mixture to about 140-175° C. while increasing the vacuum to about 1 mm Hg so as to remove by-products;
    (d) refluxing the heated reaction mixture at about 1 mm Hg for about 0.5-2 hours; and
    (e) cooling the heated reaction mixture to about 20-30° C. to yield a mixture of the polycarbonate siloxane macrodiol and said catalyst
    wherein the catalyst is inactivated in the cooled reaction mixture
    by adding water to the cooled reaction mixture, refluxing the mixture for 1 hour at about 125-140° C. at about 200 mm Hg and increasing the vacuum to about 1 mm Hg to remove the water, so as to yield the polycarbonate siloxane macrodiol.

2. A method of preparing a polyurethane elastomeric composition further comprising (f) reacting a soft segment consisting of the polycarbonate siloxane macrodiol of claim 1 having formula I(a)

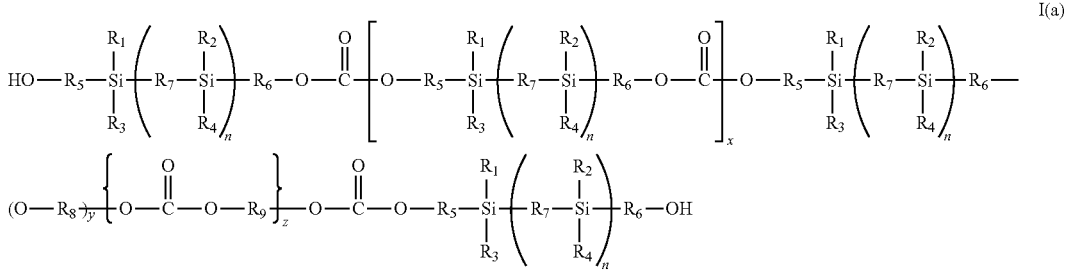

wherein $R_1$, $R_2$, $R_3$, and $R_4$ are methyl, $R_8$ is ethyl, $R_9$ is hexyl, $R_5$ and $R_6$ are propyl or butyl, $R_7$ is O or —$CH_2$—$CH_2$—, x is an integer of about 1-50, n and y are integers of 0 or more, and z is 0;
    (b) an initiator catalyst;
    (c) a diisocyanate; and
    (d) an alkylene diol chain expander, to yield the polyurethane elastomeric composition having improved mechanical properties compared to PDMS-based polyurethanes.

3. The method of claim 2, wherein the molecular weight of the polycarbonate siloxane macrodiol is 400-2000.

4. The method of claim 2, wherein the chain extender is 1,4-butane diol (BDO).

5. The method of claim 2, wherein the proportion of hard segment comprising diisocyanate and chain extender in the polyurethane is 30-60 wt-%.

6. The method of claim 2, wherein the proportion of hard segment comprising diisocyanate and chain extender in the polyurethane composition is 40-50 wt-%.

7. A medical device, article or implant which is composed wholly or partly of the polyurethane elastomeric composition made by the method of claim 2.

8. A medical device, article, or implant of claim 7 wherein said medical device, article, or implant is a cannula, extracorporeal device, artificial organ, pacemaker lead, defibrillator lead, blood pump, balloon pump, A-V shunt, biosensor, membrane for cell encapsulation, drug delivery device, wound dressing, artificial joint, orthopaedic implant, or soft tissue replacement.

\* \* \* \* \*